US011549957B2

(12) United States Patent
Sasaki et al.

(10) Patent No.: US 11,549,957 B2
(45) Date of Patent: Jan. 10, 2023

(54) AUTOMATED ANALYZER AND AUTOMATED ANALYSIS SYSTEM

(71) Applicant: Hitachi High-Technologies Corporation, Tokyo (JP)

(72) Inventors: Shunsuke Sasaki, Tokyo (JP); Kenta Imai, Tokyo (JP); Toshiharu Suzuki, Tokyo (JP); Katsuhiko Sakamoto, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 271 days.

(21) Appl. No.: 15/750,526

(22) PCT Filed: Jul. 25, 2016

(86) PCT No.: PCT/JP2016/071665
§ 371 (c)(1),
(2) Date: Feb. 6, 2018

(87) PCT Pub. No.: WO2017/033648
PCT Pub. Date: Mar. 2, 2017

(65) Prior Publication Data
US 2018/0224474 A1 Aug. 9, 2018

(30) Foreign Application Priority Data
Aug. 25, 2015 (JP) .............................. JP2015-165362

(51) Int. Cl.
*G01N 35/00* (2006.01)
*B01L 9/00* (2006.01)
(Continued)

(52) U.S. Cl.
CPC ....... *G01N 35/00584* (2013.01); *G01N 35/00* (2013.01); *B01L 3/00* (2013.01);
(Continued)

(58) Field of Classification Search
CPC .. G01N 35/00584; G01N 35/00; G01N 21/76; G01N 35/04; G01N 35/10;
(Continued)

(56) References Cited

U.S. PATENT DOCUMENTS 4,325,910 A * 4/1982 Jordan ................. G01N 21/253
250/564
5,473,551 A * 12/1995 Sato ................. G01N 35/00594
422/50

(Continued)

FOREIGN PATENT DOCUMENTS

EP 0 502 638 A2 9/1992
JP 2003-139690 A 5/2003
(Continued)

OTHER PUBLICATIONS

International Search Report (PCT/ISA/210) issued in PCT Application No. PCT/JP2016/071665 dated Nov. 1, 2016 with English translation (five pages).

(Continued)

*Primary Examiner* — Benjamin R Whatley
*Assistant Examiner* — Curtis A Thompson
(74) *Attorney, Agent, or Firm* — Crowell & Moring LLP

(57) ABSTRACT

An automated analyzer includes an analysis operation part that causes a sample and a reagent to react and based on the reaction result performs analysis of the sample, wherein: the automated analyzer includes a plurality of units constituting the analysis operation part, a temperature adjustment mechanism that heats or cools the units, a temperature sensor that measures the temperature of the units, and a control part that controls the temperature adjustment mechanism. The control part sets the measurement startable temperature range of each unit, which is the temperature range of the operation specification thereof, and the operable temperature range, (Continued)

which is a temperature range that is wider than the measurement startable temperature range, and starts the analysis process of the sample when the temperature of each unit has entered the operable temperature range.

7 Claims, 10 Drawing Sheets

(51) Int. Cl.
| | |
|---|---|
| G01N 27/327 | (2006.01) |
| G01N 33/53 | (2006.01) |
| G01N 35/10 | (2006.01) |
| G01N 35/04 | (2006.01) |
| G01J 1/32 | (2006.01) |
| G01N 21/76 | (2006.01) |
| B01L 3/00 | (2006.01) |

(52) U.S. Cl.
CPC . *B01L 9/00* (2013.01); *G01J 1/32* (2013.01); *G01N 21/76* (2013.01); *G01N 27/327* (2013.01); *G01N 33/53* (2013.01); *G01N 35/04* (2013.01); *G01N 35/10* (2013.01); *G01N 2035/00346* (2013.01)

(58) Field of Classification Search
CPC ............... G01N 33/53; G01N 27/327; G01N 2035/00346; B01L 3/00; B01L 9/00; G01J 1/32
See application file for complete search history.

(56) References Cited

U.S. PATENT DOCUMENTS

| | | | | |
|---|---|---|---|---|
| 5,482,861 | A * | 1/1996 | Clark | B01L 3/08 422/63 |
| 7,317,743 | B2 * | 1/2008 | Hofmeister | H01S 5/042 372/29.015 |
| 10,330,604 | B2 * | 6/2019 | Konishi | G01N 21/82 |
| 2005/0007042 | A1 * | 1/2005 | Moore | A01B 45/02 318/139 |
| 2006/0263258 | A1 | 11/2006 | Harris et al. | |
| 2007/0018846 | A1 * | 1/2007 | Taraian | G08C 17/02 340/5.2 |
| 2008/0089384 | A1 * | 4/2008 | Nishina | G01N 25/18 374/54 |
| 2009/0015639 | A1 * | 1/2009 | Fukui | B41J 2/0458 347/62 |
| 2010/0290952 | A1 * | 11/2010 | Koike | G01N 35/04 422/73 |
| 2011/0085916 | A1 * | 4/2011 | Talbot | F04B 49/06 417/14 |
| 2013/0224753 | A1 * | 8/2013 | Ishizawa | G01N 35/00623 435/6.12 |
| 2013/0243652 | A1 | 9/2013 | Nishigaki et al. | |
| 2014/0193893 | A1 * | 7/2014 | Ishizawa | G01N 35/04 435/287.2 |
| 2014/0295450 | A1 * | 10/2014 | Morita | C12Q 1/6886 435/6.14 |
| 2015/0104351 | A1 * | 4/2015 | Makino | G01N 35/0092 422/64 |
| 2015/0268192 | A1 * | 9/2015 | Saito | G01N 27/4067 205/793 |
| 2016/0018426 | A1 * | 1/2016 | Moriya | G01N 35/026 422/65 |
| 2017/0212137 | A1 * | 7/2017 | Sasaki | G01N 21/75 |
| 2017/0285000 | A1 * | 10/2017 | Fukuda | G01N 21/01 |

FOREIGN PATENT DOCUMENTS

| | | |
|---|---|---|
| JP | 2005-181123 A | 7/2005 |
| JP | 2006-3222 A | 1/2006 |
| JP | 2010-66108 A | 3/2010 |
| JP | 2014-81392 A | 5/2014 |
| JP | 2016-90345 A | 5/2016 |

OTHER PUBLICATIONS

Japanese-language Written Opinion (PCT/ISA/237) issued in PCT Application No. PCT/JP2016/071665 dated Nov. 1, 2016 (four pages).
Japanese-language International Preliminary Report on Patentability (PCT/IPEA/409) issued in PCT Application No. PCT/JP2016/071665 dated Jul. 12, 2017 with Annexes (10 pages).
Extended European Search Report issued in counterpart European Application No. 16838995.5 dated Mar. 28, 2019 (nine pages).

* cited by examiner

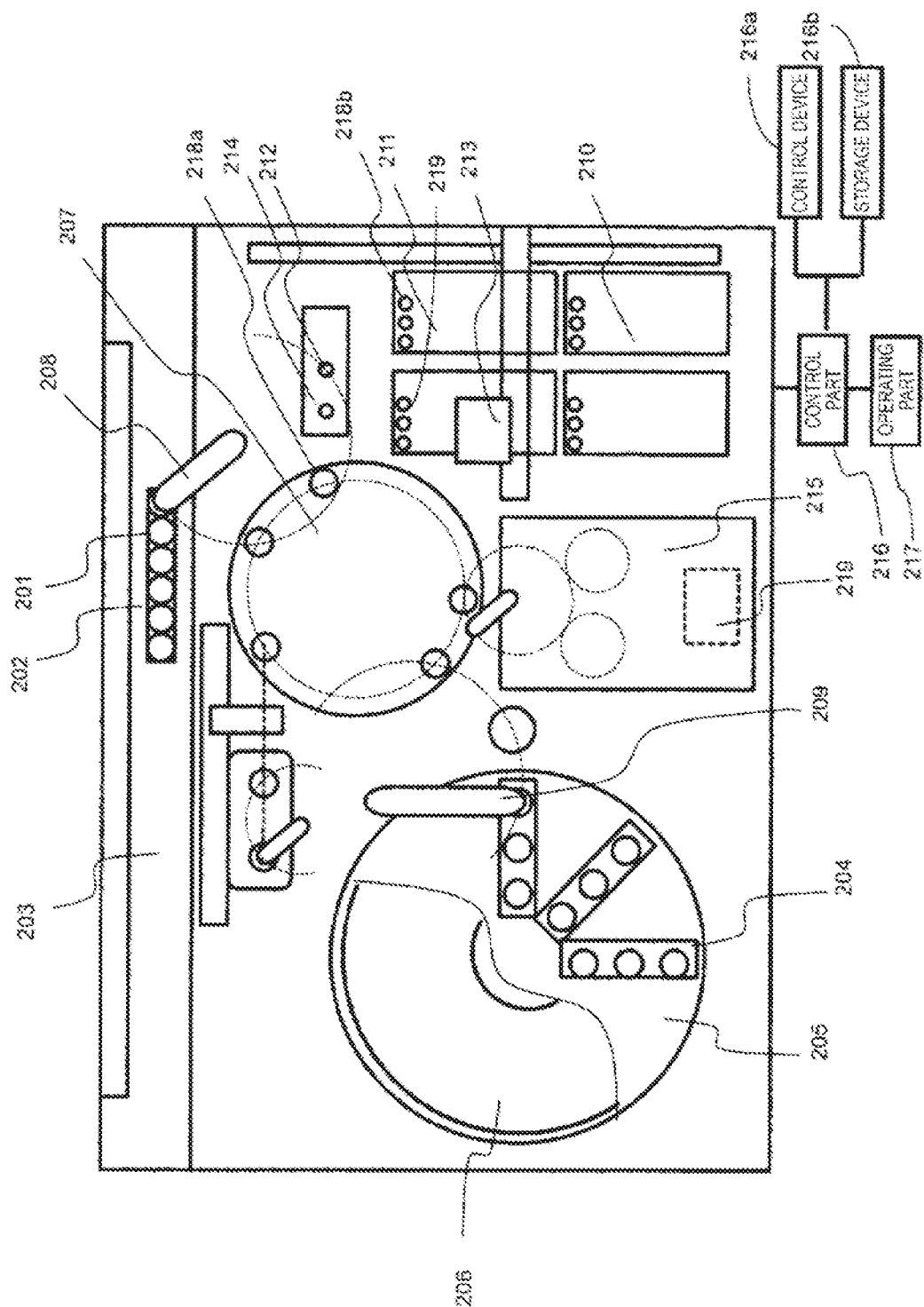
[Fig. 1]

[Fig. 2]
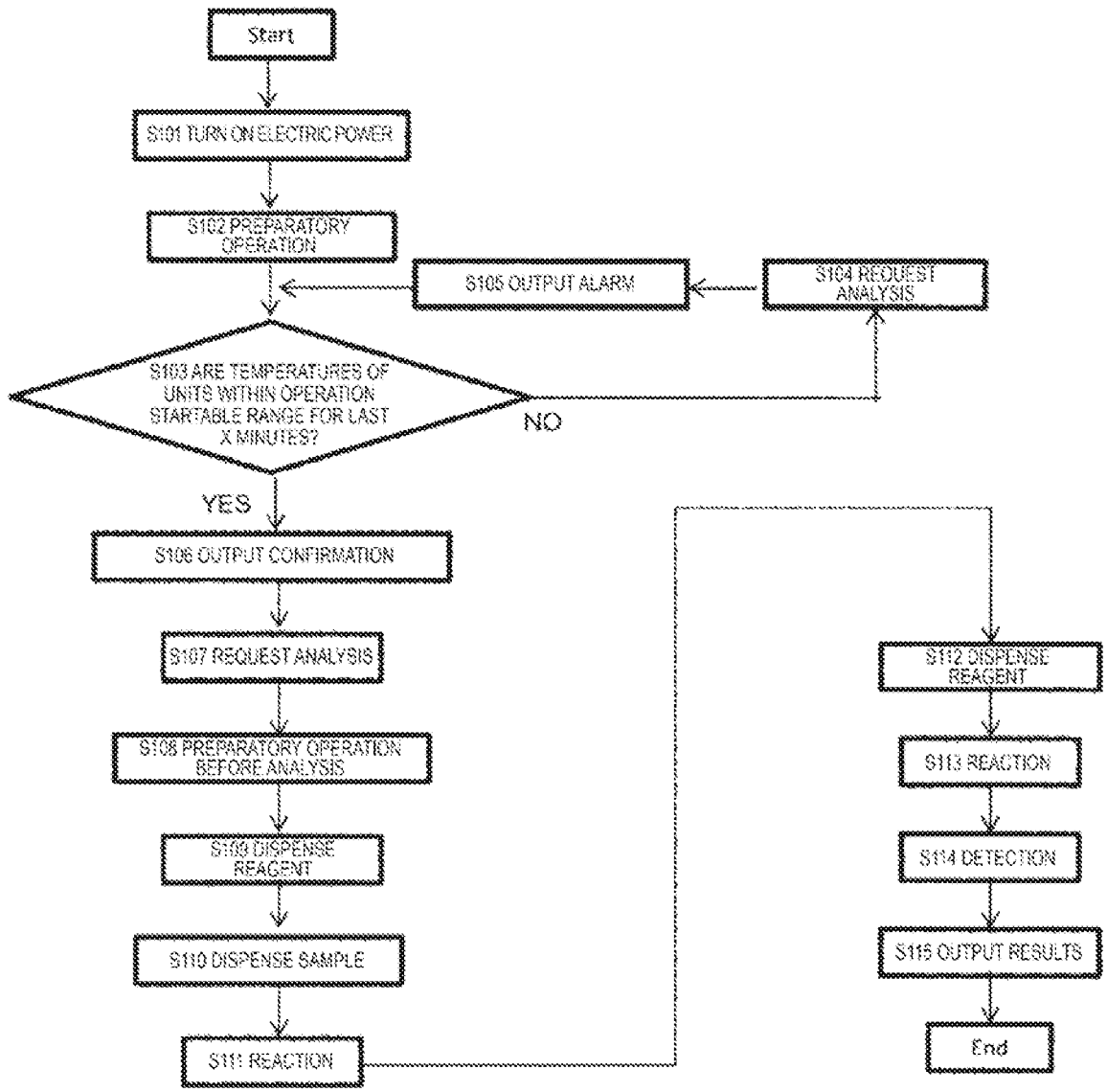

[Fig. 3]
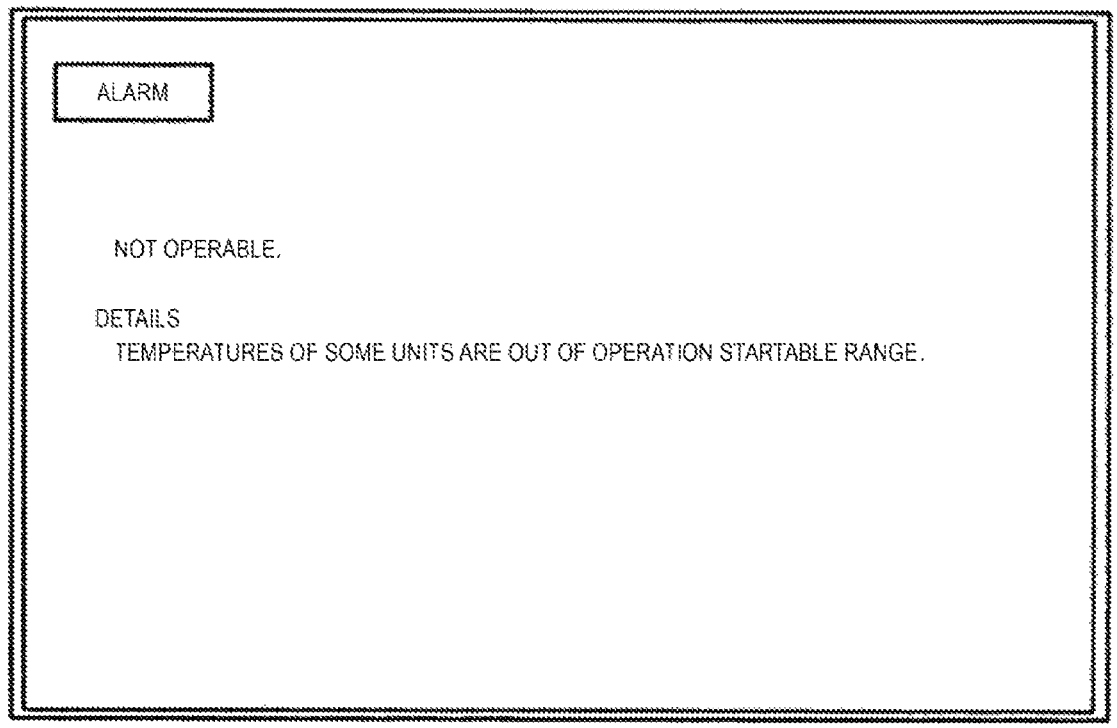
[Fig. 4]
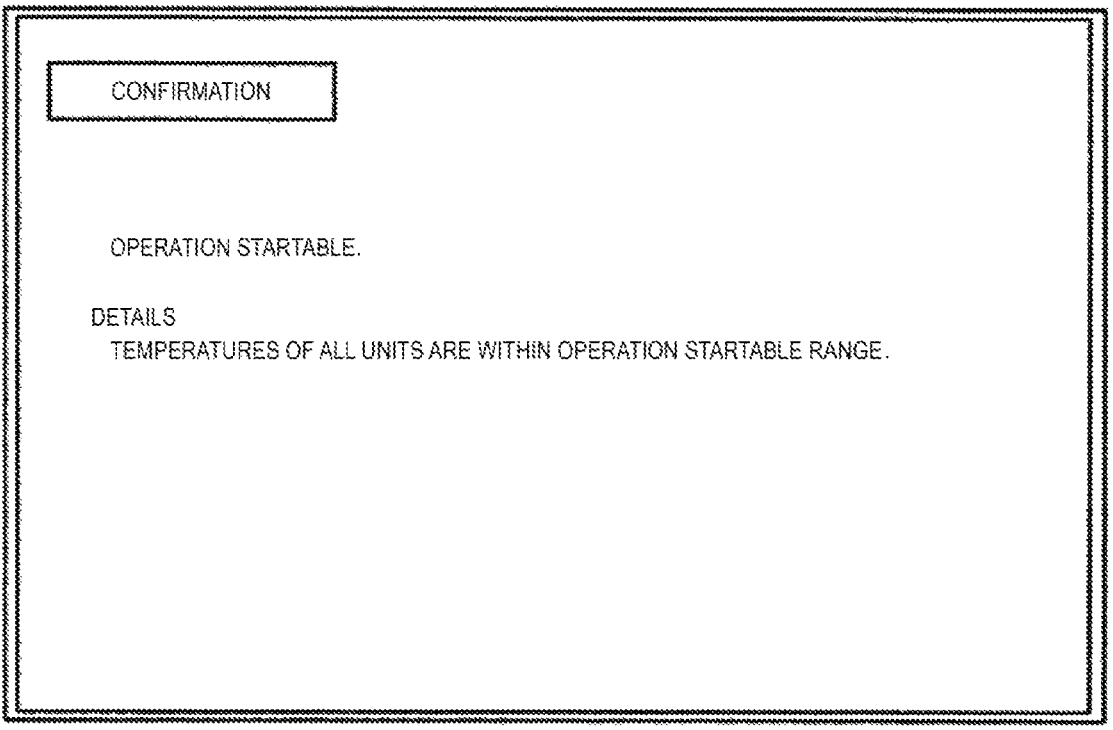

[Fig. 5]
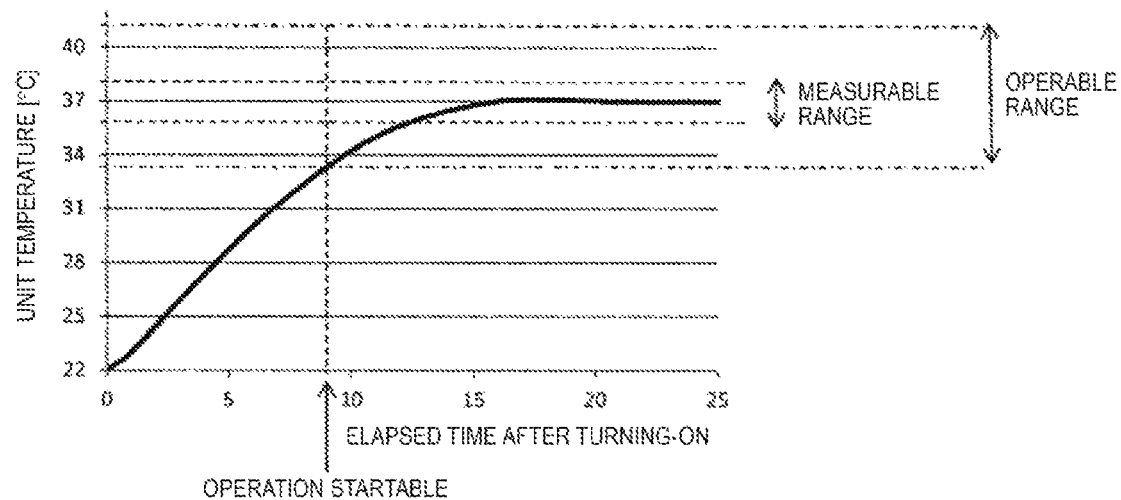
[Fig. 6]
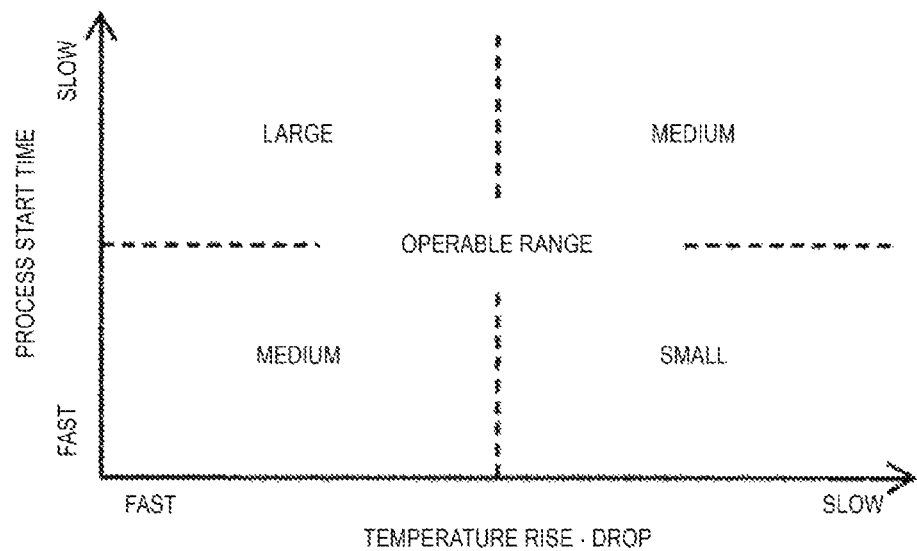

[Fig. 7]
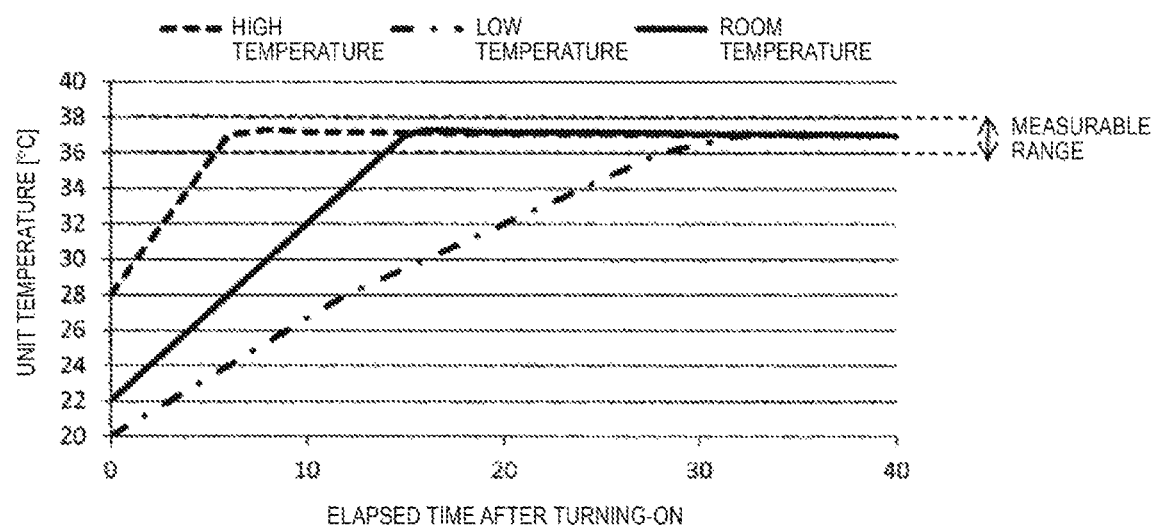

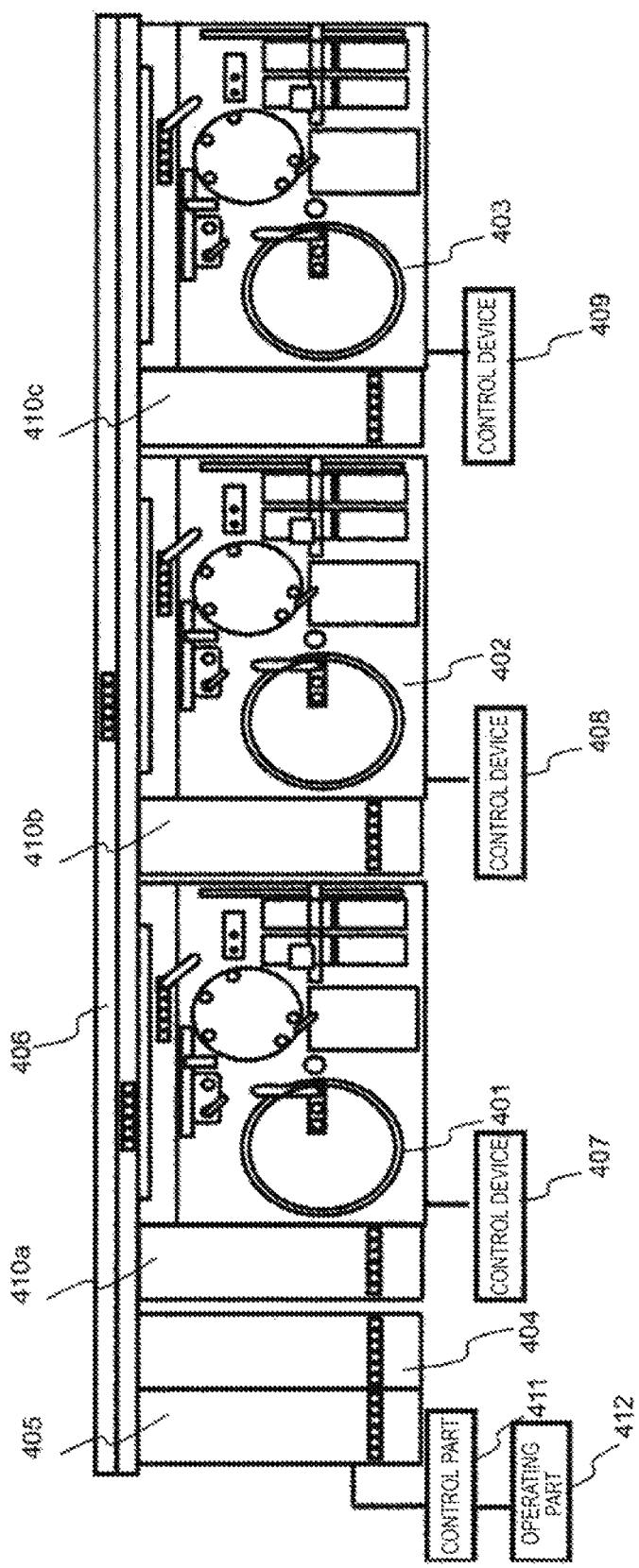

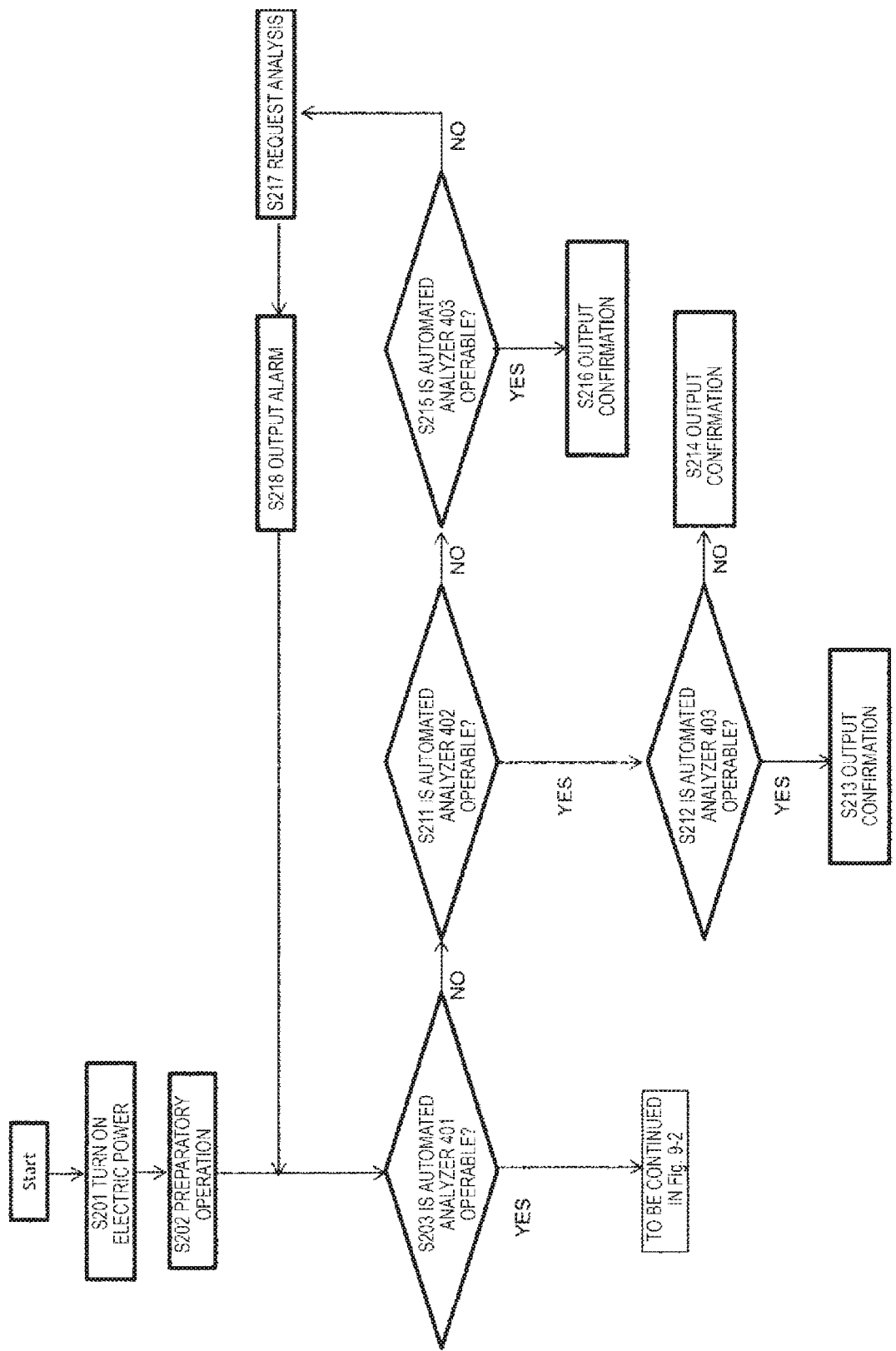
[FIG. 9A]

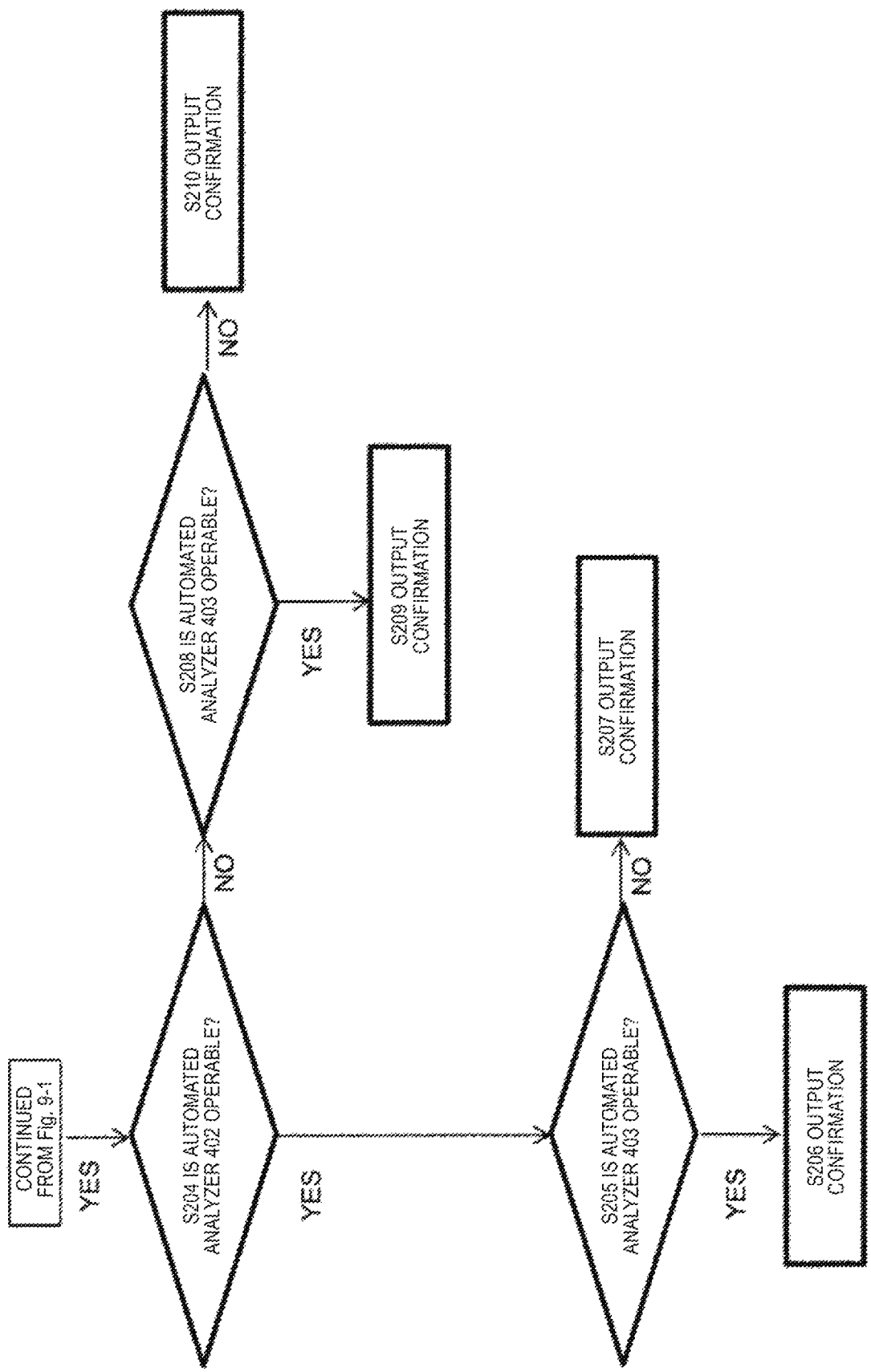
[FIG. 9B]

[FIG. 10A]
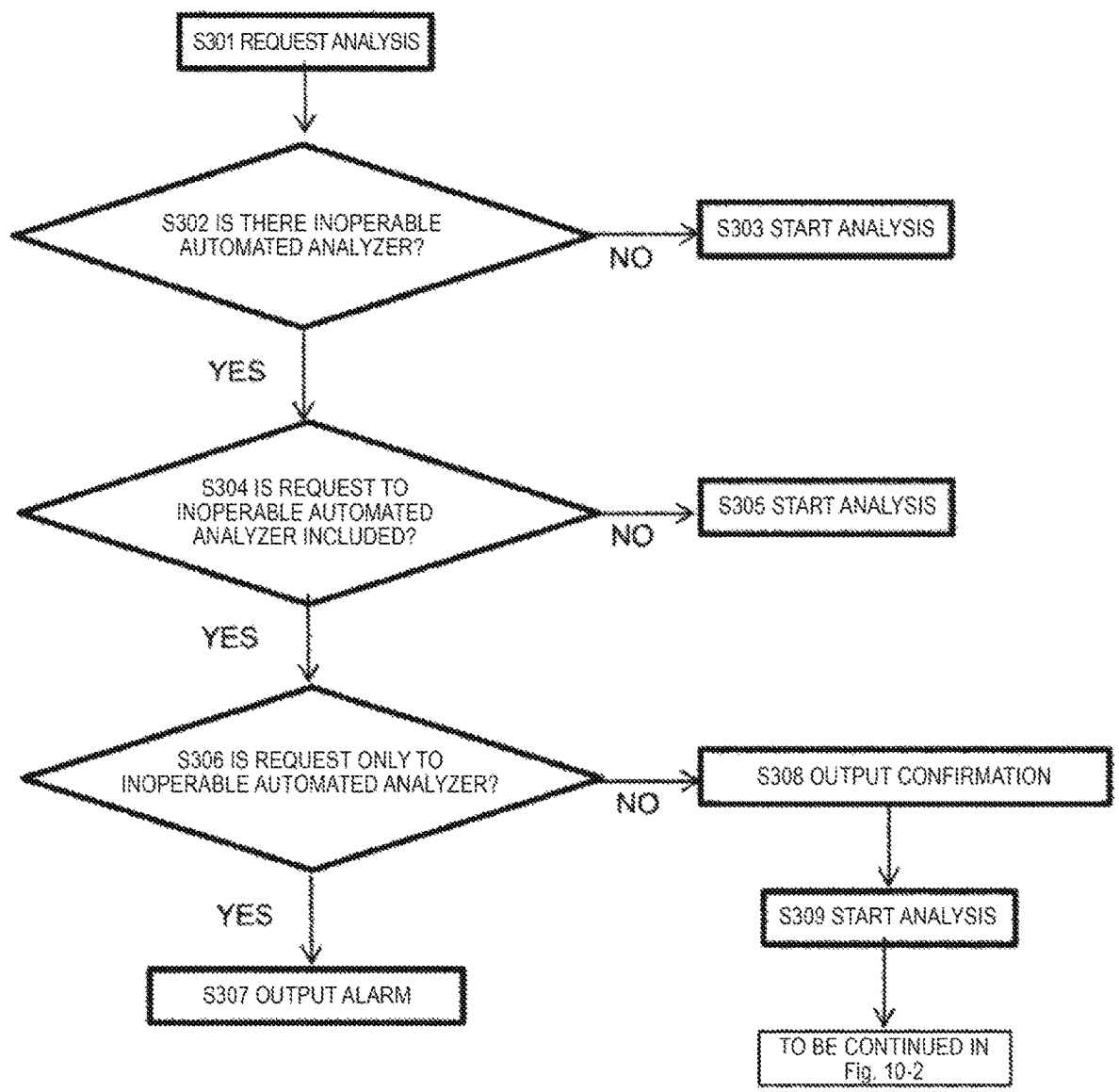

[FIG. 10B]
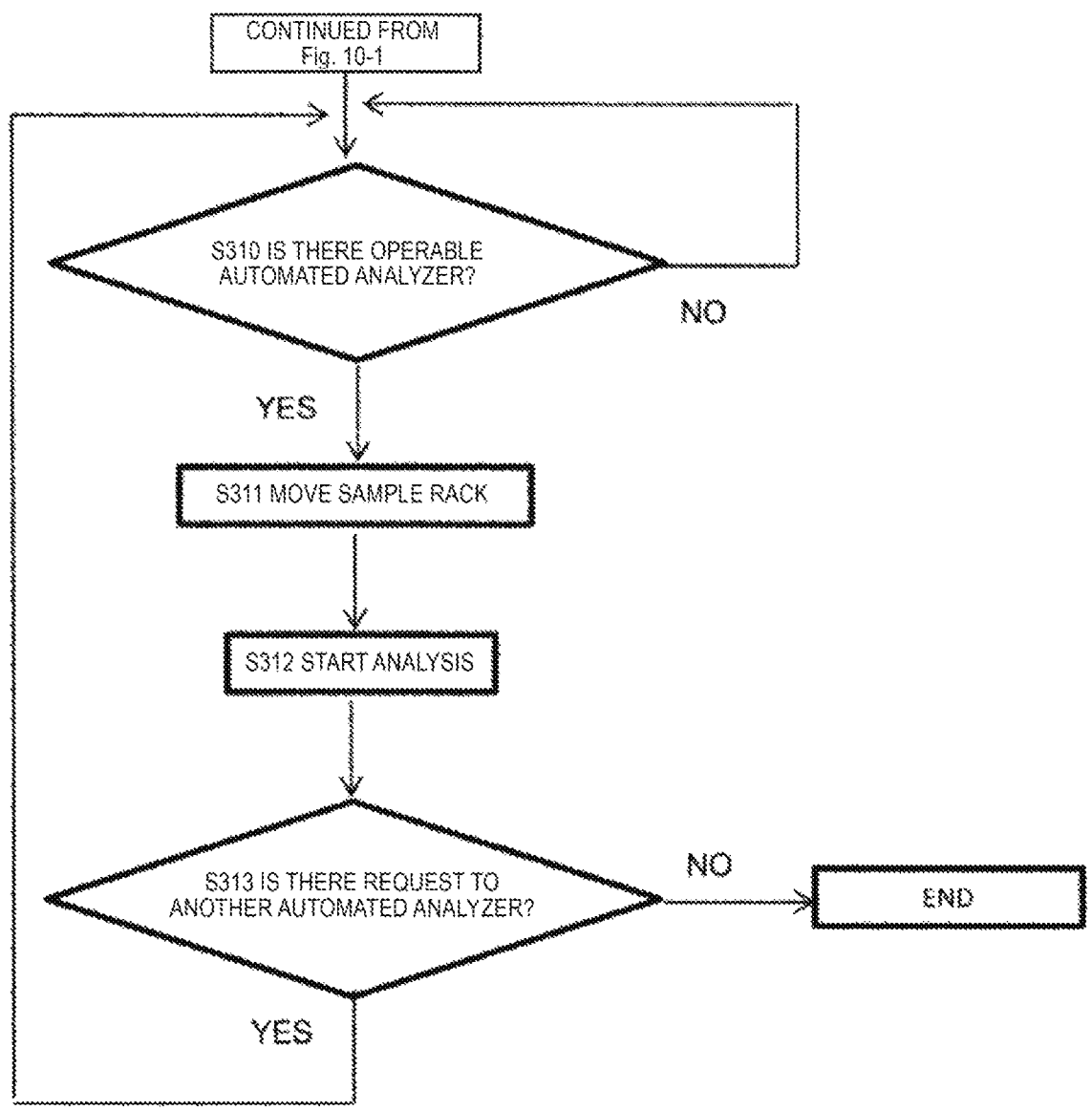

AUTOMATED ANALYZER AND AUTOMATED ANALYSIS SYSTEM

TECHNICAL FIELD

The present invention relates to an automated analyzer that analyzes a sample of blood or the like and a method for monitoring a state of the analyzer.

BACKGROUND ART

There has been an automated analyzer in the related art, which includes units having a temperature adjusting function, such as a reaction unit in which a sample reacts with a reagent and a cooling unit that keeps a reagent cool. It is necessary to wait for a start of measurement after the analyzer is turned on until the units reach a measurable temperature. In particular, a reactor or a reagent cooling unit has a large difference between a controlled temperature and the room temperature, and a period of time is taken to reach the measurable temperature.

In conventional automated analyzers, when units do not reach a measurable temperature range after the analyzer is turned on, it is not possible to start up the measurement even when there is a request for measurement, and thus a user feels significantly inconvenient.

Recently, there has been a high demand for a rapid output of an inspection result, it is necessary to keep the analyzer ON, in order to shorten a period of time taken for an output of a result even in a case of a low operation rate at night, in an emergency, or the like. On the other hand, when measurement is not performed, electric power consumed by an analyzer in a standby state increases, and thus it is not possible to satisfy a demand for reduction in inspection costs.

In a technology disclosed in PTL 1, of constituent elements of an automated analyzer, a constituent element functioning as a heat source that increases a temperature in the analyzer and a constituent element functioning as a cold source that decreases a temperature in the analyzer include an electric power switch that switches between ON/OFF of electric power and a control mechanism that controls an ON/OFF operation of the electric power switch provided for each constituent element, according to a plurality of start modes. In a preheat starting mode included in the plurality of starting modes, the constituent element functioning as the heat source keeps operating during a pause before the start of the analyzer, thereby, maintaining a state in which a temperature of a reactor or in the analyzer is higher than a temperature thereof during a pause in a normal start mode and causing the analyzer to more rapidly transition to standby than in the normal start mode after the start of the analyzer.

CITATION LIST

Patent Literature

PTL 1: JP-A-2014-81392 (Specification of US Patent Application Publication No. 2013/0243652)

SUMMARY OF INVENTION

Technical Problem

In the technology disclosed in PTL 1, it is necessary to operate the constituent element functioning as the heat source even during the pause before the start of the analyzer, and thus electric power is consumed even while a user recognizes that the electric power of the analyzer is being turned off.

In addition, a measurement result within a predetermined period of time from the start of the analyzer is considered to be a measurement result obtained in a state in which temperature of the analyzer is unstable, and data thereof may be flagged. However, in this method, data obtained in a state in which temperature is stable and data obtained in a state in which temperature is unstable are present together in flagged data, and thus there is a problem in that a user has to perform measurement of flagged data again after all.

The purpose of the present invention is to provide an automated analyzer that keeps the costs required for inspection to a minimum and is capable of starting measurement immediately after being turned on.

Solution to Problem

In order to solve the problem described above, an automated analyzer according to the present invention includes a plurality of units constituting an analysis operation part, a temperature adjustment mechanism that heats or cools the units, a temperature sensor that measures the temperature of the units, and a control part that controls the temperature adjustment mechanism, and the control part sets a measurement startable temperature range of each unit, which is the temperature range of the operation specification thereof, and an operable temperature range, which is a temperature range that is wider than the measurement startable temperature range, and starts the analysis process of the sample when the temperature of the unit has entered the operable temperature range of the unit.

Advantageous Effects of Invention

According to the present invention, it is possible to provide the automated analyzer that keeps the costs required for inspection to a minimum and is capable of starting the measurement immediately.

BRIEF DESCRIPTION OF DRAWINGS

FIG. 1 is a schematic diagram of an automated analyzer.

FIG. 2 is a flowchart designating a schematic control flow of the automated analyzer from turning-on of electric power of the analyzer to an end of analysis.

FIG. 3 illustrates an example of an alarm screen output when there is a measurement request in a state in which the temperature of some units is out of an operation start temperature range.

FIG. 4 illustrates an example of a confirmation screen output when the temperatures of all units have entered the operation start temperature range.

FIG. 5 is a graph illustrating a relationship between the unit temperature and a period of time after the analyzer turns on.

FIG. 6 is a graph illustrating a concept of a method for determining an operable range.

FIG. 7 is a graph illustrating a relationship between unit temperature and a period of time after turning on when the temperature is different during turning on.

FIG. 8 is a diagram schematically illustrating a system in which a plurality of automated analyzers are connected.

FIG. 9A is a flowchart illustrating a control flow in a module type automated analysis system in which the plurality of automated analyzers are connected.

FIG. 9B is a flowchart illustrating the control flow in the module type automated analysis system in which the plurality of automated analyzers are connected.

FIG. 10A is a flowchart illustrating an operation flow in the automated analysis system when there is an analysis request in a state in which there is a non-operable automated analyzer.

FIG. 10B is a flowchart illustrating the operation flow in the automated analysis system when there is an analysis request in a state in which there is a non-operable automated analyzer.

DESCRIPTION OF EMBODIMENTS

Hereinafter, embodiments of the present invention will be described with reference to the accompanying figures.

In this example, an automated analyzer is described as an example. Examples of the automated analyzer include an automated biochemical analyzer or an automated immunological analyzer. However, this is only an example of the present invention, and the present invention is not limited to an embodiment which will be described below and widely includes analyzers that causes a sample and a reagent to react and analyzes the sample based on a result of the reaction. For example, the present invention also includes a mass spectroscope or a coagulation analyzer that measures blood coagulation time used in clinical inspection. In addition, the present invention is also applicable to a combined system of the automated biochemical analyzer and the automated immunological analyzer or an automated analysis system to which the analyzers are applied.

Example 1

FIG. 1 is a schematic diagram of the automated analyzer to which an analyzer monitoring method of the example is applied.

In FIG. 1, the automated analyzer includes a rack conveying line 203 that conveys a rack 202, a reagent cooling unit 205, an incubator disk (reaction disk) 207, a sample dispensing mechanism 208, a reagent dispensing mechanism 209, and a detector unit 215. The constituent elements described above are referred to as units, in some cases. Units such as the reagent cooling unit 205, the incubator disk (reaction disk) 207, the detector unit 215, and an auxiliary reagent temperature adjusting unit 219 are provided with temperature adjustment mechanisms that heat or cool respective units and a temperature sensor that measures the temperature of the unit. Hereinafter, units provided with the temperature adjustment mechanism as described above are collectively referred to as a temperature adjusting function assigned unit. The temperature adjustment mechanisms are controlled by a control part 216.

The rack 202 stores a plurality of sample containers 201 containing a biological sample (sample) such as blood or urine and is conveyed over the rack conveying line 203 in a state of storing the sample containers 201. The reagent cooling unit 205 is a reagent container storing unit and stores/cools a plurality of reagent containers 204 containing various types of reagents used in analysis of the sample. At least a part of the top surface of the reagent cooling unit 205 is covered with a reagent disk cover 206. The incubator disk 207 is provided with a reaction container arranged portion in which a plurality of reaction containers 218a for causing a sample and a reagent to react are arranged and a temperature adjustment mechanism that adjusts the temperature of the reaction container 218a to a predetermined temperature. The sample dispensing mechanism 208 includes a rotational drive mechanism or a vertical drive mechanism and is capable of dispensing the sample from the sample container 201 to the reaction container 218a contained in the incubator disk 207 by using the drive mechanisms. In addition, the reagent dispensing mechanism 209 also includes a rotational drive mechanism or a vertical drive mechanism and dispenses a reagent from the reagent container 204 to the reaction container 218a contained in the incubator disk 207 by using the drive mechanisms. The detector unit 215 includes a photomultiplier tube, a light source lamp, an optical spectrometer, or a photodiode, has a function of adjusting the temperatures thereof, and analyzes a reaction solution.

Further, the automated analyzer includes a reaction container/dispensing tip storing unit 211 storing a plurality of unused reaction containers 218b or dispensing tips 219, standby reaction container/dispensing tip storing unit 210 for replacement/supplement thereof, a discarding hole 212 for discarding the dispensing tip 219 and the reaction container 218 after use thereof, and a conveyance mechanism 213 that grips and conveys the dispensing tip 219 and the reaction container 218.

The conveyance mechanism 213 is provided to movable in X-axis, Y-axis, and Z-axis directions (not illustrated) and conveys the reaction container 218b stored in the reaction container/dispensing tip storing unit 211 to the incubator disk 207, discards the reaction container 218 after use to the discarding hole 212, or conveys unused dispensing tip 219 to the tip mounting position 214.

In the automated analyzer, the rack conveying line 203, the reagent cooling unit, the incubator disk 207, the sample dispensing mechanism 208, the reagent dispensing mechanism 209, the detector unit 215 that performs analysis of a reaction solution, the conveyance mechanism 213, and the like described above are referred to as an analysis operation part.

Further, the automated analyzer includes a control device (control part) 216 that controls an overall operation of the automated analyzer and an operating part 217, in addition to the analysis operation part described above. For example, the control part 216 is made of a hardware board and is connected to a control device 216a such as a computer or a storage device 216b such as a hard disk. The operating part 217 is configured to include a display unit such as a display or an input device such as a mouse or a keyboard. For example the storage device 216b stores temperature ranges associated with respective units. The control part 216 or the control device 216a may be configured of hardware by a dedicated circuit board or may be configured of software executed by a computer connected to the automated analyzer. In a case of a configuration by the hardware, the control part or device can be realized by integrating a plurality of computing elements that execute processes on a wiring board, or in a semiconductor tip or a package. In a case of a configuration by the software, the control part or device can be realized by mounting a high speed general-purpose CPU in a computer and executing a program that executes desired arithmetic processing. An existing device can be upgraded by a recording medium in which the program is recorded. Also, the apparatus, the circuit, and the computer are connected via a wired or wireless network and data is appropriately transmitted and received therebetween.

Next, a monitoring method or an analysis operation of a state of the analyzer after turning-on of electric power performed in the automated analyzer will be described.

FIG. 2 is a schematic flowchart from the turning-on of electric power of the analyzer to an end of analysis performed in the automated analyzer illustrated in FIG. 1.

First, a user performs turning-on of electric power (S101). The automated analyzer performs a preparatory operation (S102) such as replacement of system water that flows in the analyzer or an operation check of each unit (S102). After the preparatory operation (S102) is ended, the control device 216a regularly monitors the temperatures of the temperature adjusting function assigned unit such as the reagent cooling unit 205, the incubator disk 207, or the detector unit 215, compares the temperatures to an operation startable range that is stored in the storage device 216b, and checks whether or not the temperature of the temperature adjusting function assigned unit is within the operation startable range for last five minutes (S103). At this time, X is independently set to the temperature adjusting function assigned units. In addition, X may be automatically set depending on the external temperature. At this time, when the temperature of any one of the temperature adjusting function assigned units is out of the operation startable range, the control part 216 does not start measurement even when there is an analysis request (S104) by an operator and displays an alarm (S105) on a display of the operating part 217 as illustrated in FIG. 3. On the other hand, when the control device 216a determines that all of the temperature adjusting function assigned units are in an operable range, the confirmation (S106) is displayed on the display of the operating part 217 as illustrated in FIG. 4, and the user is notified that the unit is operable.

Then, when there is an analysis request (S107) from the user, the control part 216 performs a pre-analysis preparatory operation (S108) in which the operation check of the sample dispensing mechanism 208, the reagent dispensing mechanism 209, and the detector unit 215 are performed. Subsequently, the reagent dispensing mechanism 209 suctions a first reagent by the reagent container 204 stored in the reagent cooling unit 205 and dispenses the reagent to the reaction container 218a disposed in the incubator disk 207 by the conveyance mechanism 213 (S109). The sample dispensing mechanism 208 suctions a sample from the sample container 201 and dispenses the sample to the reaction container 218a in which the reagent is dispensed in S109 (S110). Then, the reaction container 218a is on standby on the incubator disk 207 for a predetermined period of time and a reaction step of performing reaction between the sample and the first reagent (S111) is performed. Substantially, the reagent dispensing mechanism 209 dispenses a second reagent to the reaction container 218a (S112). Then, the reaction container 218a is on standby again on the incubator disk for the predetermined period of time and a reaction step of performing reaction between the reaction solution and the second reagent (S113) is performed. Then, the detector unit 215 detects concentration of sample components in the reaction solution in the reaction container 218a (S114). Based on the concentration of the sample components detected by the detector unit, the control part 216 displays a result on the display of the operating part 217 (S115), and the measurement process is ended.

Next, in FIG. 5, a relationship between an operation startable temperature range and a measurable temperature range.

A target temperature ±a with respect to the target temperature of the temperature adjusting function assigned units is a measurable range, and the target temperature ±β(α<β) is an operation startable range. The measurable range is the temperature range of the operation specification of each unit and means a range in which the temperature of the temperature adjusting function assigned units is controlled in order to output an appropriate measurement result. On the other hand, the operation startable range is a temperature range that is adjustable in the measurable temperature range in a period of time to the actual use of the temperature adjusting function assigned unit as a target. The measurable temperature range and the operation start temperature range are set in advance and are stored in the storage device 216b.

After the analyzer turns on, the units start temperature control such that the temperatures of the units are within the measurable range. Since the external temperature is different from the temperature of the measurable range of the units normally, a certain period of time is taken until the temperatures of the units are stably within the measurable range. In an example of FIG. 5, elapsed time of 13 minutes after the turning-on, the temperature is within the measurable range (for example 37° C.±1° C. in FIG. 5); however, the unit is not used for four minutes after the analysis request (S107) as a start point. In this example, when the temperature range, in which the temperature is adjustable for four minutes, is 3° C., it is possible to start the process of the analysis request (S107) from a stage of nine minutes after the turning-on, actually without waiting for 13 minutes after the turning-on. Hence, an operable range can be obtained by adding, to the measurable range, a temperature adjustable range within a predetermined period of time from transmission of the analysis request (a start of the analysis process) to an actual use of the units. In other words, in the example in FIG. 5, the operable range is 33° C. to 41° C. obtained from 37° C.±1° C. (measurable range)±3° C. (a temperature adjustable range within the predetermined period of time from the transmission of the analysis request to the actual use of the units. Hence, when the temperature of the unit has entered the operable temperature range (when reaching 33° C. in the example in FIG. 5), it is possible to start the analysis of the sample. In particular, one of the characteristics of the example is as follows. Even when temperature of the unit is out of the measurement startable temperature range and within the operable temperature range, it is possible to start the analysis of the sample. The confirmation illustrated in FIG. 4 is displayed in S106 and the user may be notified that it is possible to start the analysis of the sample.

Here, a concept of a method for determining the operation startable range is described by using FIG. 6. First, the measurable temperature range is determined depending on the specification of each unit. On the other hand, the operation startable range is determined, depending on a period of time to the actual use of the units and a period to time taken for a temperature change (temperature rise or drop) per a unit temperature in the units. More specifically, when the long period of time from the analysis request (S107) as the start point to the use of the units is taken, the operation startable range is increased. In addition, in a case of considering the temperature characteristics of the units and a unit for which a period of time for temperature rise or fall is needed, the operation startable range is decreased.

When the temperature of the unit is out of the measurement startable range in a state in which the analysis operation is started in the units, an alarm is output. Further, a flag is attached to a sample processed in the unit in a time zone in which the temperature of the unit is out of the measurement startable range, and thus the user pays attention to the sample.

In addition, a period of time taken for the unit to reach the measurable range from the operation startable range is different depending on an ambient temperature of a place at which the unit is disposed.

FIG. 7 is a graph schematically illustrating a relationship between the unit temperature and the time elapsed after turning on when the ambient temperature is different.

For example, in a unit having the measurable range of 36 to 38° C., a period of time to reach the measurable range is shortened when the temperature is high in the environment, that is, when the temperature is close to the measurable range (dashed line in FIG. 7). Therefore, it is possible to set the wide operation startable range. On the other hand, when the temperature is low in the environment, that is, when the temperature is far apart from the measurable range (dot-and-dash line in FIG. 7), the reach to the measurable range is delayed and thus it is necessary to set a narrow operation startable range.

Therefore, the control part 216 monitors the temperature of the environment in which the analyzer is disposed and sets the operable range according to the ambient temperature. More specifically, the operation startable range is set by being automatically selected from a plurality of operation startable ranges stored in the storage device 216b according to the ambient temperature.

According to the example, by adding a concept of the operation startable temperature range to a temperature monitoring method of the automated analyzer, it is possible to start the measurement without waiting until the unit a unit having fast temperature rise/drop or the unit used later in the analysis process enters the measurement range.

In other words, by using the temperature monitoring method of the example, no measurement request is made until the temperatures of hitherto all of the units reach the measurable range, and thus it is possible to shorten the period of time taken for an output of a result to the shortest extent according to the temperature characteristics or ambient temperature of the analyzer. Therefore, the analyzer does not need to be in a standby state in which electric power turns on in the time period in which an operation rate is low at night or in an emergency, and thus it is possible to perform inspection at the minimum cost without power consumption during the standby state.

Example 2

Next, an example of the temperature monitoring method in the module type automated analysis system of a plurality of connected automated analyzers is described. The entire configuration of the automated analyzer, configurations of the control device 216a, the storage device 216b, and the operating part 217 are the same as those in Example 1. Hereinafter, the description of the same portions as those in Example 1 is omitted.

FIG. 8 is a schematic diagram illustrating a system in which the plurality of automated analyzers of Example 1 are connected. Automated analyzers 401, 402, and 403 have the same configuration as an example described in Example 1, and automated-analyzer control devices 407, 408, and 409 similar to the control device 216a and sample standby buffers 410a, 410b, and 410c that process measurement standby sample are provided for the respective devices. In addition, the system includes a sample loading unit 404 that loads a sample, a sample storing unit 405 that accommodates a sample after the analysis, a sample rack conveying unit 406 that conveys a sample mounted on the rack, and a system control part 411 and a system operating part 412.

Similar to the control part 216 of Example 1, the system control part 411 is configured by a program that is executed on a hardware board or on a computer and controls operation states of the overall automated analysis system and the plurality of automated analyzers. In addition, similar to Example 1, the system operating part 412 includes a display unit such as a display and an input device such as a mouse or a keyboard.

Next, a temperature monitoring method in the related art when the system, in which a plurality of the automated analyzers 401, 402, and 403 are connected, performs the analysis will be described.

In the system hitherto, the entire system does not operate if the units in all of the automated analyzers in the system do not reach the measurement temperature range. In other words, also when the automated analyzer 401 reaches the measurement temperature range, and measurement of only the automated analyzer 401 is requested, the system is not started and it is not possible to start the measurement if the other automated analyzers 402 and 403 reach the measurement temperature range. Therefore, the automated analyzer in which a period of time is taken to reach the measurement temperature range is detached from the system once and the measurement is started by only the other automated analyzers, or samples, which are measured by the plurality of analyzers and samples, which are not measured, are not present together in the sample rack, and the like. In this manner, a decrease in throughput is caused.

Next, temperature monitoring methods of each automated analyzer and the system in the example will be described.

The temperature monitoring of each of the automated analyzers is the same as that in Example 1 by the automated-analyzer control devices 407, 408, and 409. The system control part 411 monitors states of the automated analyzers and determines whether or not the automated analyzers are operable.

FIGS. 9-1 and 9-2 illustrate the control flow in the module type automated analysis system in which the plurality of automated analyzers are connected. After the user turns on the electric power (S201), the automated-analyzer control devices 407, 408, and 409 perform the preparatory operation (S202). Then, the system control part 411 checks whether or not the automated analyzers 401, 402, and 403 are operable. Hereinafter, the automated-analyzer control devices 407, 408, and 409 monitor the temperature state of the unit in each automated analyzer as described in Example 1, and determines whether or not the temperature enters the operable range. When the temperature enters the operable range, information that the automated analyzer is operable is output to the system control part 411. The system control part 411 determines whether or not the automated analyzers are operable based on the information.

The system control part 411 checks whether or not the automated analyzer 401 is operable (S203). When the automated analyzer 401 is operable, subsequently the system control part 411 determines whether or not the automated analyzer 402 is operable (S204). When the automated analyzer 402 is operable, the system control part 411 determines whether or not the automated analyzer 403 is operable (S205). When the automated analyzer 403 is operable, the system control part 411 outputs, to the system operating part 412, confirmation indicating that the automated analyzers 401, 402, and 403 are operable (S206), and the operation is started. When the automated analyzer 403 is not operable, the system control part 411 outputs, to the system operating part 412, confirmation indicating that only the automated analyzers 401 and 402 are operable (S207), and operations of only the automated analyzers 401 and 402 are started.

When the automated analyzer 402 is determined not to be operable in S204, the system control part 411 determines whether or not the automated analyzer 403 is operable in S208. When the automated analyzer 403 is operable, the system control part 411 outputs, to the display unit of the system operating part 412, confirmation indicating that the automated analyzers 401 and 403 are operable (S209), and operations of only the operable automated analyzers 401 and 403 are started.

When the automated analyzer 403 is not operable in S208, the system control part 411 outputs, to the display unit of the system operating part 412, confirmation indicating that only the automated analyzer 401 is operable (S210), and the operation of only the operable automated analyzer 401 is started.

When the automated analyzer 401 is not operable in S203, the system control part 411 determines whether or not the automated analyzer 403 is operable in S211. When the automated analyzer 402 is operable, determination of whether or not the automated analyzer 402 is operable is determined in S212, and confirmation indicating that the automated analyzers 402 and 403 are operable is output to the system operating part 412 in S213 in a case where the automated analyzer 402 is operable (S213). The operations of only the operable automated analyzers 402 and 403 are started.

When the system control part 411 determines that the automated analyzer 403 is not operable in S212, the confirmation indicating that only the automated analyzer 402 is operable is output in S214 to the system operating part 412 (S214), and the operation of only the operable automated analyzer 402 is started.

When the system control part 411 determines that the automated analyzer 402 is not operable in S211, subsequently, determination of whether or not the automated analyzer 403 is operable is performed in S215. When the automated analyzer 403 is operable in S215, the system control part outputs, to the system operating part 412, confirmation indicating that the automated analyzers 403 is operable (S216), and operations of only the operable automated analyzers 403 is started.

In the other hand, after the system control part 411 determines that the automated analyzer 403 is not operable in S215, the system control part 411 outputs an alarm indicating that there is no operable automated analyzer on the display unit of the system operating part 412 in a case where there is an analysis request from the user (S217), and the analysis request is not received.

In conclusion, the flowcharts illustrated in FIGS. 9-1 and 9-2, the system control part 411 determines whether or not the automated analyzers 401, 402, and 403 are operable, and possibility of the operation is displayed on the display unit. As described in Example 1, whether or not the automated analyzer is operable is determined by determining whether or not the temperature of the temperature adjusting function assigned units of the automated analyzer enters the operable temperature range.

After the electric power turns on, the system control part 411 regularly performs the monitoring flowchart illustrated in FIGS. 9-1 and 9-2 until a period of automatically determined time elapses. In addition, when there is an automated analyzer that is not operable even after a predetermined time point passes, the temperature adjusting function assigned unit that is a cause of non-operation outputs an alarm indicating a temperature abnormality.

In addition, only the automated analyzer in a non-operable state is only checked without determining whether or not the automated analyzers determined once by the system control part 411 are operable.

Next, an operation of the system when there is a request of analysis in a state in which there is a non-operable automated analyzer.

FIGS. 10-1 and 10-2 are operation flowcharts of the system when there is an analysis request in a state in which there is a non-operable automated analyzer.

After the system control part 411 receives the analysis request in S301, the system control part checks that there is a non-operable automated analyzer in the automated analyzers in the system in S302. The check may be performed as illustrated in FIGS. 9-1 and 9-2.

When there is no non-operable automated analyzer, the analysis is started in S303. On the other hand, when there is a non-operable automated analyzer, a check of whether or not the analysis requests include a request analysis to the non-operable automated analyzer in S304. When the analysis requests do not include a request analysis to the non-operable automated analyzer, the analysis is started in S305. When the analysis requests include a request analysis to the non-operable automated analyzer, the system control part 411 checks whether or not the analysis request of S301 is only the analysis request to the non-operable automated analyzer in S306. When the analysis requests in S301 are only the analysis requests to the non-operable automated analyzers, the system control part 411 outputs, to the display unit of the system operating part 412, an alarm indicating that it is not possible to start the analysis in S307. On the other hand, when the analysis requests in S301 includes a request to another automated analyzer, the system control part 411 outputs, to the system operating part 412, confirmation indicating that the request to the operation non-startable automated analyzer is included in S308, and the operation startable automated analyzer is prioritized to be subjected to the analysis in S309.

After the process of the sample is ended in S309, the system control part 411 checks again whether there is an automated analyzer that has become operable in the system in S310. When there is an automated analyzer that has become operable, the sample rack moves to the automated analyzer in S311 and analysis is started in S312. When the analysis is ended, whether or not there is a request to another automated analyzer for the corresponding sample in S313 is checked. When there is a request to another automated analyzer for the corresponding sample, S310 to S313 are repeatedly performed. When the measurement of the sample is ended, the sample rack is conveyed to the sample storing unit 405.

In addition, when there is no automated analyzer that has become operable in the system in S310, the check of S310 is regularly repeated.

According to the example, when the operable automated analyzer and the non-operable automated analyzer are present together in the same system, only the operable automated analyzer can perform the analysis process without detaching the non-operable automated analyzers are detached from the system. In addition, for a sample with measurement requests to both of the operable automated analyzer and non-operable automated analyzer, the analysis by the non-operable automated analyzer is postponed, and the analysis by the measurement startable automated analyzer is prioritized. In this manner, it is possible to make the output of the result faster than that in the related art.

The present invention is not limited to the examples described above and includes various modification examples. For example, the examples are described in detail for easy understanding of the present invention, and the present invention is not absolutely limited to inclusion of the entire configuration described above. Also, it is possible to replace a part of a configuration of an example with a configuration of another example, and it is possible to add a configuration of an example to a configuration of another example. Also, it is possible to perform addition/removal/replacement of a part of each of the configurations of the examples to/from/with another configuration. Also, a part or the entirety of the configurations, the functions, the processing units, processing means, or the like may be realized by hardware by designing an integrated circuit, for example. Also, the configurations, the functions, and the like described above may be realized with software by analyzing and performing programs by which processors realize respective functions.

It is possible to place information of the programs, tables, files, or the like that realize the functions in a recording device such as a memory, a hard disk, a solid state drive (SSD) or a recording device such as an IC card, an SD card, an optical disk, or the like.

In addition, control wires or information wires are illustrated when the wires are considered to be necessary for description, and all of the control wires or the information wires are not absolutely illustrated for a product. Actually, almost all of the configurations may be considered to be connected to each other.

REFERENCE SIGNS LIST

201: sample container
202: rack
203: rack conveying line
204: reagent container
205: reagent cooling unit
206: reagent disk cover
207: incubator disk
208: sample dispensing mechanism
209: reagent dispensing mechanism
210: reaction container/dispensing tip storing unit
211: reaction container/dispensing tip storing unit
212: discarding hole
213: conveyance mechanism
214: tip mounting position
215: detector unit
216: control part
216a: control device
216b: storage device
217: operating part
218a: reaction container
218b: reaction container
219: auxiliary reagent temperature adjusting unit
401, 402, 403: automated analyzer
404: sample loading unit
405: sample storing unit
406: sample conveying line
407, 408, 409: automated-analyzer control device
410: sample standby buffer
411: system control part
412: system operating part

The invention claimed is:

1. An automated analyzer that causes a sample and a reagent to react and, based on a reaction result, performs analysis of the sample, the automated analyzer comprising:
an analysis operation part that includes a plurality of units, the plurality of units including a reagent cooling unit, an incubator disk, and a detector;
a plurality of temperature adjustment mechanisms disposed in the plurality of units that heat or cool the plurality of units individually;
a temperature sensor provided in each of the plurality of units that measures a unit temperature of each of the plurality of units; and
a control part that controls the plurality of temperature adjustment mechanisms individually,
wherein the control part sets a measurement startable temperature range of each of the plurality of units, which is a temperature range in which the plurality of units are configured to output an appropriate measurement result, and an operable temperature range, which is a temperature range that is wider than and includes the measurement startable temperature range, for the plurality of units individually,
wherein the control part is configured to issue an output confirmation, process a request for the analysis and to start, in response to the analysis request from a user, a pre-analysis preparatory operation of the sample in response to a determination by the control part that unit temperatures of all of the units included in the plurality of units have entered the operable temperature range while continuing to control the plurality of temperature adjustment mechanisms such that the unit temperature of each of the plurality of units reaches the measurement startable temperature range, wherein the pre-analysis preparatory operation includes an operation check of each of the plurality of units, and
wherein the control part is configured to adjust the operable temperature range for each of the plurality of units based on the unit temperature thereof, wherein the operable temperature range is widened in a case where the unit temperature is closer to the measurement startable temperature range upon turning on the automated analyzer and narrowed in a case where the unit temperature is farther apart from the measurement startable temperature range upon turning on the automated analyzer.

2. The automated analyzer according to claim 1, wherein a plurality of reaction containers that store the sample are arranged in the incubator disk, a temperature adjustment mechanism of the plurality of temperature adjustment mechanisms that is disposed in the incubator disk controls a temperature of the incubator disk, a temperature adjustment mechanism of the plurality of temperature adjustment mechanisms that is disposed in the reagent cooling unit is capable of cooling a plurality of reagents, and a temperature adjustment mechanism of the plurality of temperature adjustment mechanisms that is disposed in the detector is capable of adjusting the temperature of the detector.

3. The automated analyzer according to claim 1, wherein the control part starts the analysis of the sample when the temperatures of all of the plurality of units are within the operable temperature range.

4. The automated analyzer according to claim 1, further comprising: a display unit, wherein the control part displays on the display unit that the analysis of the sample is startable.

5. The automated analyzer according to claim 4, wherein the control part displays an alarm on the display unit when the temperature of any of the plurality of units departs from the measurement startable temperature range after the analysis of the sample is started, and displays a flag with a result of a measurement processed in a period during which the temperature departs from the measurement startable temperature range.

6. An automated analysis system in which a plurality of the automated analyzers of claim 1 are connected, the automated analysis system comprising:
a first automated analyzer of the plurality of automated analyzers;
a second automated analyzer of the plurality of automated analyzers; and
a system control part that controls the automated analysis system and operating states of the plurality of respective automated analyzers,
wherein the system control part determines whether or not the first or second automated analyzer is operable based on information from the first and second automated-analyzer control parts and, in a case in which at least one of the first automated analyzer and the second automated analyzer is operable, operates the at least one of the first automated analyzer and the second automated analyzer depending on an operability thereof and an analysis request received by the at least one of the first automated analyzer and the second automated analyzer, and in a case in which neither of the first automated analyzer and the second automated analyzer is operable, the system control part outputs an alarm indicating an impossibility to start the analysis.

7. The automated analysis system according to claim 6, wherein, in a case that the analysis request is made to the first automated analyzer and the second automated analyzer for a same sample, and the first automated analyzer is operable but the second automated analyzer is not operable, the system control part gives priority to the first automated analyzer and starts the analysis of the sample from the first automated analyzer, and wherein, after the analysis of the sample has ended in the first automated analyzer, whether or not the second automated analyzer is operable is again determined.

* * * * *